United States Patent [19]
Ellingson et al.

[11] 3,940,619
[45] Feb. 24, 1976

[54] METHOD FOR PRODUCING THREE-DIMENSIONAL REAL IMAGE USING RADIOGRAPHIC PERSPECTIVE VIEWS OF AN OBJECT

[75] Inventors: William A. Ellingson; Alvin A. Read, both of Ames, Iowa

[73] Assignee: Iowa State University Research Foundation, Inc., Ames, Iowa

[22] Filed: May 30, 1974

[21] Appl. No.: 474,591

[52] U.S. Cl. .................................. 250/313; 350/3.5
[51] Int. Cl.² ......................................... G02B 27/00
[58] Field of Search .............. 250/313, 524; 350/3.5

[56] References Cited
UNITED STATES PATENTS

| | | | |
|---|---|---|---|
| 3,675,012 | 7/1972 | Derderian et al. | 350/3.5 |
| 3,746,872 | 1/1973 | Ashe et al. | 250/313 |
| 3,788,726 | 1/1974 | Groh et al. | 250/313 |
| 3,843,225 | 10/1974 | Kock et al. | 250/313 |

FOREIGN PATENTS OR APPLICATIONS

| | | | |
|---|---|---|---|
| 1,931,298 | 1/1970 | Germany | 350/3.5 |

OTHER PUBLICATIONS
"Holographic Stereogram from Sequential Component Photographs", McCrickerd et al., App. Physics Letters, Vol. 12, No. 1, 1-1-68, pp. 10 to 12.

*Primary Examiner*—James W. Lawrence
*Assistant Examiner*—B. C. Anderson
*Attorney, Agent, or Firm*—Dawson, Tilton, Fallon & Lungmus

[57] ABSTRACT

A sequence of separate radiographs are made by indexing a radiation source along a known path relative to the object under study. Thus, each radiograph contains information from a different perspective. A holographically-recorded image is then made from each radiographic perspective by exact re-tracing of the rays through each radiographic perspective such that the re-tracing duplicates the geometry under which it was originally prepared. The holographically-stored images are simultaneously illuminated with the conjugate of the reference beam used in the original recordings. The result is the generation of a three-dimensional real image of the object such that a light-sensitive device can be moved to view the real image along any desired surface with the optical information in all other surfaces greatly suppressed.

4 Claims, 5 Drawing Figures

3,940,619

METHOD FOR PRODUCING THREE-DIMENSIONAL REAL IMAGE USING RADIOGRAPHIC PERSPECTIVE VIEWS OF AN OBJECT

The invention described herein was made at least partially in the course of, or under, a contract with the U.S. Atomic Energy Commission.

BACKGROUND AND SUMMARY

The present invention relates to a system for tomosynthesis of a radiopaque object or model using optical holography; more particularly, it relates to a method for producing a real image of the object using radiographic perspective views of the object from which holographic images are recorded. The real image of the object can then be viewed along any desired plane by using a light-sensitive device. That is, the real image may then be subject to tomographic scanning without destroying or detracting from the information available. The present invention is useful in the field of non-destructive testing, for example, of a fuel core for a nuclear reactor. The invention also has widespread use in the medical field for the viewing or profiling of internal organs. One of the advantages of the present invention in the medical field is that only a single set of radiographic perspectives need be taken to generate the real image of the object under study. This exposes the patient to substantially less ionizing radiation than in some prior art methods.

The following patent and publications are representative of work done in this general area: (1) Derderian, et al., U.S. Pat. No. 3,675,012 for "Cinefluorographic Holography", issued July 4, 1972; (2) Groh and Kock, MATERIALS RESEARCH BY HOLOGRAPHY, "Non-Destructive Testing", Vol. 5 October, 1972, p. 301–302; (3) Kock and Tiemens, "Tomosynthesis a Holographic Method for Variable Depth Display", OPTICS COMMUNICATIONS, Vol. 7, March, 1973, p. 260–265; (4) Grant, "Tomosynthesis; a Three-Dimensional Radiographic Imaging System", IEEE TRANSACTIONS ON BIOMEDICAL ENGINEERING, Vol. 19, January, 1972, p. 20–28; and (5) Chau, "Three-Dimensional Reproduction of Shadowgrams", OPTICS COMMUNICATIONS, Vol. 4 September, 1971, p. 1–4.

In the present invention, a sequence of individual radiographs of the object are made by indexing a source of radiation along a known path. At each stop along the path a radiograph is taken on previously unexposed medium. As the radiation source progresses, an unexposed section of the medium is also advanced. Thus, there are produced a series of radiographs, each containing information concerning the object from a different perspective. These radiographs are sometimes referred to herein as "radiographic perspectives".

Each radiographic perspective is then recorded on holographic medium by exact re-tracing of the original ray paths through each radiographic perspective to duplicate the geometry under which it was originally prepared. More specifically, each radiographic perspective is illuminated by a source of coherent light through a ray backtracing lens to form an object beam. Thus, a shadowgraphic image of the radiographic perspective is projected onto a holographic medium together with a reference beam of light for the exposure. The ray back-tracing lens and object beam source are changed for each exposure to exactly duplicate the geometry under which the radiographic perspective then being holographically recorded was made. During the holographic recording, the angle of the reference beam relative to the recording medium is maintained constant. Thus, there are produced a number of separate holographically-recorded images, each corresponding to an associated radiographic perspective and containing the same optical perspective information that its associated radiographic perspective contained.

The holographically-recorded images are simultaneously illuminated with a source of coherent light from a direction exactly opposite to that used to make the recordings. Such a beam is known in the art as a "conjugate" beam. By this one means, for example, that the conjugate of a diverging beam is a converging beam whose rays exactly re-trace the rays of the diverging beam back to their point of origin and vice versa. The conjugate of a parallel beam is another parallel beam going in exactly the opposite direction relative to the orientation of the holographic recording medium.

All of the individual holographically-recorded images are then projected into space to reconstruct the real image of the original object in three dimensions. Viewing of the real image may be accomplished by any number of means, such as intercepting it with a ground-glass screen, a photographic plate, a television camera or other photosensitive device. The real image may be viewed along any arbitrary planar or non-planar surface. On such a surface, the several holographically-recorded perspectives integrate to yield a clear image of the details of the object corresponding to that portion of the surface intersecting the image while details about the object at other points are suppressed.

Other features and advantages of the present invention will be apparent to persons skilled in the art from the following detailed description of one embodiment wherein identical reference numerals will refer to like parts in the various views.

THE DRAWING

FIG. 3 is a schematic view illustrating apparatus for holographically-recording images of the radiographic perspectives under conditions which permit exact ray retracing of the radiographs;

FIG. 5 is a schematic diagram of apparatus for reconstructing a three-dimensional real image from the holographically-recorded images.

DETAILED DESCRIPTION

Figure 1:
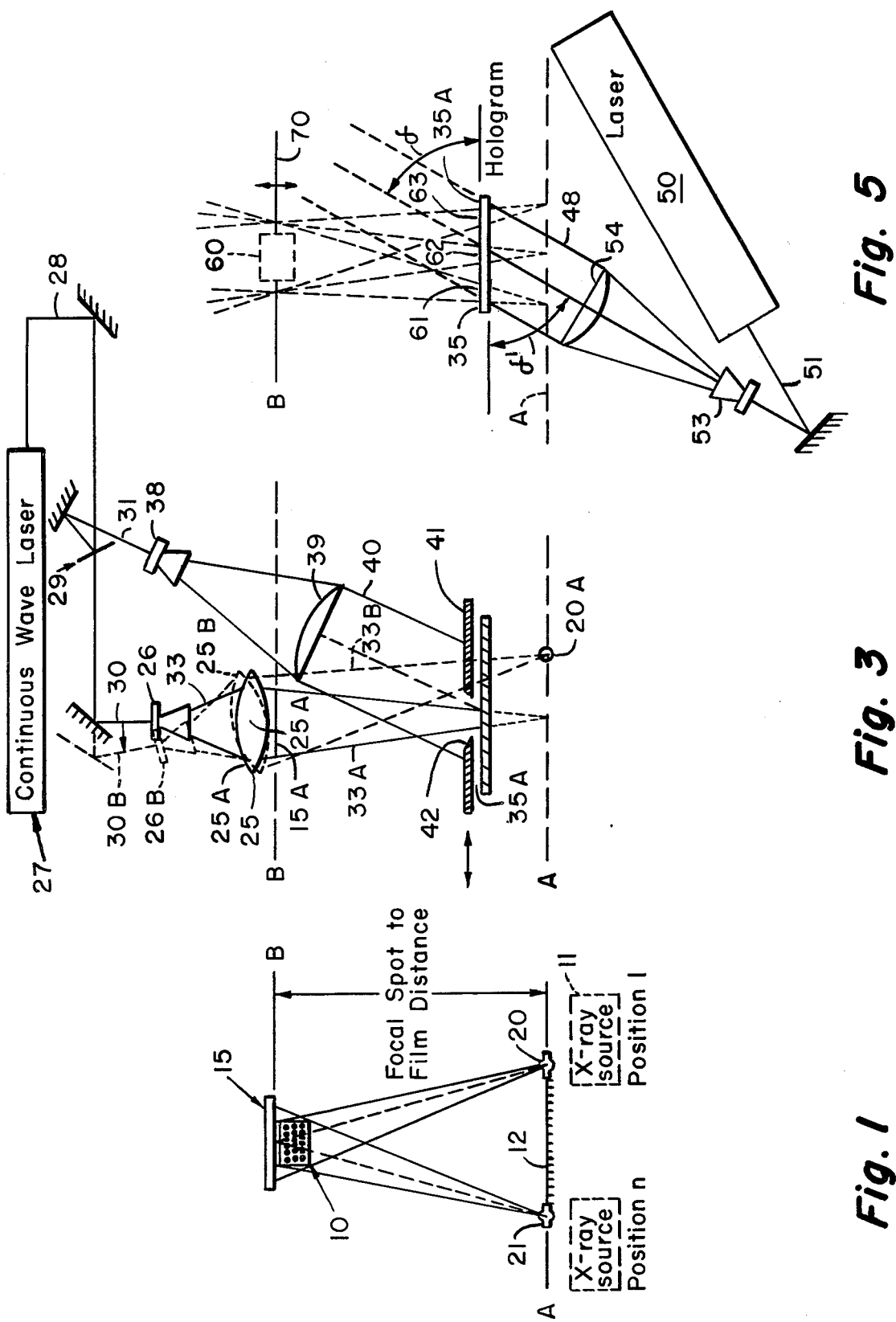
FIG. 1 is a schematic diagram of apparatus used to generate a sequence of two-dimensional radiographic perspectives using an indexed linear scan of an X-ray source.
Figure 2:
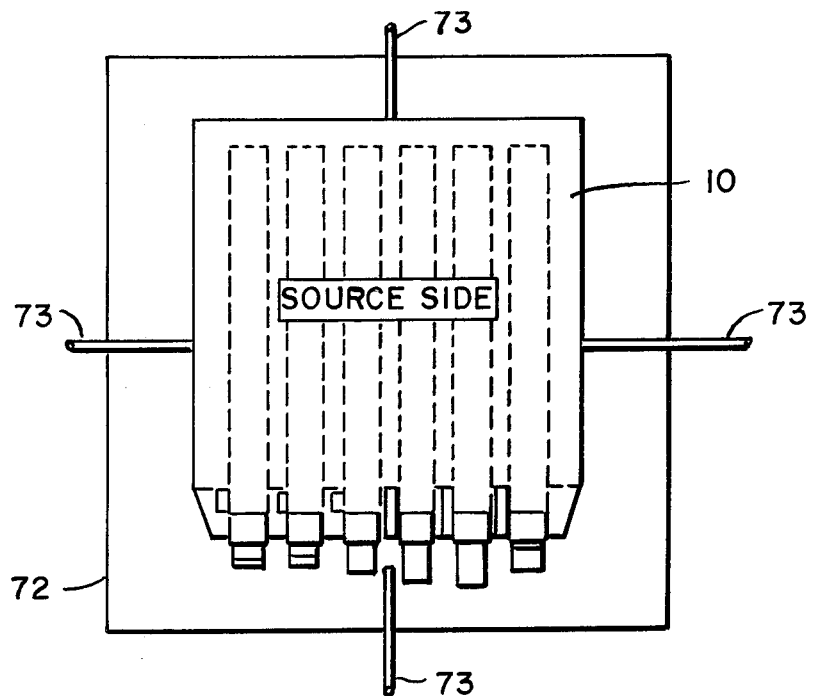
FIG. 2 is a perspective view of one method of mounting the object under study.

Before discussing the details of the invention, it is deemed advisable to have an overall picture of the various steps involved in generating a three-dimensional real image of any three-dimensional object, sometimes referred to as a "model", which is generally designated by reference numeral 10 in FIGS. 1 and 2. As illustrated, the object 10 is a model of a fuel core sub-assembly as might be used in a nuclear reactor. One of the important features of the invention, however, is that it is not so limited, but has a broad range of applications such as in fields of non-destructive testing and medicine.

Briefly, then, as shown in FIG. 1, a source of radiation 11 (such as X-rays, gamma rays, neutrons or other penetrating rays) is indexed along a path or locus 12, and at each of a number of predetermined locations along the path 12, the object 10 is exposed to the source 11. Each radiograph thus formed contains information from a different perspective of the object 10—hence, they are referred to as "radiographic perspectives".

A holographic recording is then made of each radiographic perspective by re-tracing optical light rays through each radiographic perspective such that the re-tracing duplicates the paths of the radiation which originally generated the perspective, as seen in FIG. 3, wherein a single radiographic perspective is designated 15A, and the holographic recording medium is denoted 35.

The several holographically-recorded images are then simultaneously illuminated, as shown in FIG. 5, with a beam of coherent light 48 which impinges on the holographic plate 35 from a direction which is exactly opposite to that used to make the recordings. All of the individual holographically-recorded images are then projected into space where their results add to produce a three-dimensional real image of the object as at 60. Once a three-dimensional real image of the object is formed, a ground-glass screen or a photosensitive device may be used to view the image along any desired surface. The optical information along that surface will be in sharp focus, whereas the optical information along all other surfaces is suppressed.

Returning now to FIG. 1, located behind the object 10 is a radiographic recording medium, e.g. a film cassette generally designated 15. The recording medium 15 is also indexed as the source 11 is moved so that each radiographic perspective appears as a separate record. All of these recorded perspectives are related, as will be discussed later, in such a manner that the orientation of the object relative to the recordings and the source may be reproduced.

For purposes of later reference, A designates a path 12 along which the source 11 moves. Similarly, a plane designated B illustrates the surface on which the radiographic perspectives are projected.

As will be discussed later, the path 12 of the radiation source 11 need not necessarily be a straight line, and the number of intermediate exposure positions (indicated by the hash marks between a START position 20 and an END position 21) depends upon the application and the amount of resolution that is ultimately desired.

Thus, the result of FIG. 1 is the production of a radiographic record bearing a series of individual radiographs each of which represents the object 10 irradiated from a different perspective, as determined by the indexing positions on the path 12.

Referring now to FIG. 3, the next step in the method is to produce a holographic recording comprising a sequence of individual holograms each of which contains a record of the information on a corresponding radiographic perspective, as generated in FIG. 1. It is important that the geometry used in generating each individual holographic recording be the same as was used in producing its associated radiographic perspective because the perspective information contained in the radiograph is then stored in the hologram associated therewith. This process of exactly reconstructing the geometry used for making the radiographs, in recording the holograms, is referred to as "ray back-tracing" or "retracing" since the original path of rays are re-traced from the image (i.e., the radiographic perspective) back to the source and intercepted at an intermediate location by the holographic recording medium.

In FIG. 3, an individual radiographic perspective is designated by reference numeral 15A; and the earlier identified reference path A and surface B are also indicated and separated by the same distance as were the corresponding path and surface used in making the radiographic perspectives. It will be observed that in FIG. 3, reference surface B contains the radiographic perspective and A is a path on which the rays through that perspective would converge. A converging lens 25 (sometimes referred to as the "ray back-tracing" lens) is interposed between a spatial filter 26 and the radiographic perspective 15A. A laser, designated by reference numeral 27, is used as a source of coherent light. A beam of light produced by laser 27 is designated 28; and it is split into an object beam 30 and a reference beam 31.

The object beam 30 has a small diameter, and it is diverged by the spatial filter 26 while maintaining its coherent characteristics. The divergent beam, 33, is then converged by the lens 25 to form convergent beam 33A which converges onto the path A. A holographic recording medium 35 intercepts the converging object beam emanating from the lens 25 after it has illuminated the radiograph 15A.

The reference beam 31 is diverged by means of a spatial filter 38 and then directed by means of a lens 39 into reference beam 40. A translatable opaque mask 41 having an aperture 42 is interposed in the path of the two beams 33A and 40 such that only a portion of the holographic recording medium 35 is exposed at any one time. The object here is to expose to the reference beam only that portion of the recording medium on which the shadowgraphic image of the radiographic perspective falls. In the illustrated embodiment, the reference beam 40 is collimated, but it could equally well be a convergent or a divergent beam.

As indicated above, as each individual radiographic perspective 15A is replaced by the next in the sequence (as taken in accordance with the disclosure associated with FIG. 1), the opaque mask 41 is translated to expose a different portion of the holographic film plate 35. In addition, and this is an important aspect of the present invention, the geometry of the holographic production system is restructured so as to duplicate in reverse the original geometry under which the associated radiograph was produced. In the case of the illustrated embodiment where the original path 12 of the radiation source 11 was a straight line the focused points in path A in FIG. 3 lie in a straight line. Whatever the geometry of the path 12, it will be reproduced correspondingly in the holographic recording geometry as a locus on which the object beam converges.

In order to reproduce the geometry in the illustrated embodiment, the "ray back-tracing" lens 25 is rotated about an axis 25A extending perpendicular to the plane of the page of FIG. 3 and the spatial filter 26 is rotated correspondingly while, at the same time, moved relative to the lens 25 in such a manner as to converge the object beam 33A onto the path A. Thus, to holographically record the next radiographic perspective, the converging beam 33A is translated to that indicated by the dashed lines 33B; the ray back-tracing lens 25 is rotated to the position shown in dashed line at 25B; and the spatial filter 26 is moved to the position diagrammatically illustrated by the dashed line 26B in order to satisfy the requirements indicated above. For each holographic image thus recorded, the converging object beam produced by the ray back-tracing lens takes the same geometrical path as the radiation beam used to produce the radiographic perspective that is associated with it. To insure that the object beam converges at the location corresponding to that from which the radiation source transmitted to form the radiograph, a marker may be placed on the path A of FIG. 3 with index marks at the locations corresponding to the exposure positions of FIG. 1. For example, the first radiograph was taken in an indexed position corresponding to 20A on the path A of FIG. 3. The object light beam, of course, contains the shadowgraphic image of the radiographic perspective which it illuminates.

Still referring to FIG. 3, the angle designated $\alpha$ is maintained constant. This is the angle between the axis of the reference beam 40 and the surface 35A of the holographic recording medium 35. A second angle, designated $\beta$ in FIG. 3, is the angle between the axis of the reference beam 40 and the axis of the object beam 33A. The angle $\beta$ varies according to the position at which the perspective being recorded was originally taken.

Not only is it necessary that the geometry used in making the holographic images duplicate that originally used in forming the radiographic perspectives, but it is important that the orientation of each individual radiograph 15A be maintained in the same angular and spatial relationship to each of the other radiographs as was maintained in the original recordings of the radiographs. This may be accomplished, as will be discussed in detail, by using a system of fiducial marks.

In summary, what is produced by the apparatus schematically illustrated in FIG. 3 is a single holographic record comprising a sequence of holographically-stored images, each corresponding to an associated radiographic perspective. It is from the sequence of holographically recorded images on the plate 35 that the three-dimensional real image of the original object is reconstructed, in accordance with the apparatus of FIG. 5.

The holographic record, bearing as it does a number of discrete holographically-stored images, is placed in the position as shown at 35 in FIG. 5. The holographic record bearing all of the stored images is then illuminated by the conjugate of the reference beam--that is, the beam of light 48, is directed in a direction opposite to that of the reference beam used in producing the sequence of holographic images relative to the surface 35A of the holographic record 35. The angle $\alpha$ in FIG. 5 is the same as shown in FIG. 3; and the angle $\alpha'$ in FIG. 5 is the angle $\alpha$ plus 180°.

The beam of light 48, may be generated by a laser designated 50, having output beam 51 which is diverged by the spatial filter 53 and redirected by lens 54.

The path A and surface B shown in FIGS. 1 and 3 are reproduced in FIG. 5 in the same relative relationship to one another. The holographic recording medium 35 will have the same relative position to path A of FIG. 5 as it did in FIG. 3.

The beam of coherent light 48 passes through all of the individual holographically-stored images on the plate 35 simultaneously. This means the separately recorded, individual images on the plate 35 are as mentioned above all simultaneously illuminated in FIG. 5 by the beam 48 which is the conjugate of the reference beam used in recording. The transmitted light forms a reconstructed, three-dimensional real image of the object indicated by the reference numeral 60. In other words, if three individual holographically-recorded images, each bearing its own perspective relation to the original model are designated respectively 61, 62 and 63 in FIG. 5, are all simultaneously illuminated as illustrated, the transmitted diffracted light from each image forms the composite real image 60. As a result of having a three-dimensional real image, as distinguished from a virtual image, at the location 60, a ground-glass screen or a photo-sensitive medium or device can be moved into the real image 60 where it may be used to view any desired internal portion of the object. In other words, if, for example, a photographic film is placed along the plane 70, only that particular plane will appear to be sharp in the photograph and all other planes will be blurred. That is to say, the visual information in all planes is greatly suppressed.

The plane 70, it will be observed, may take on a different orientation than that shown (it may be rotated about an axis perpendicular to the plane of the page of FIG. 5, translated or translated and rotated as long as the viewing plane remains within the real image). Furthermore, a series of photographs could be taken or a photosensitive device could be moved to any other plane of observation without diminishing or destroying the reconstructed three-dimensional real image. Thus, once the real image is reconstructed, that real image can be scanned at will, using any arbitrarily shaped surface in any arbitrary orientation and with any number of photo-sensitive or photo-recording devices.

Figure 4:
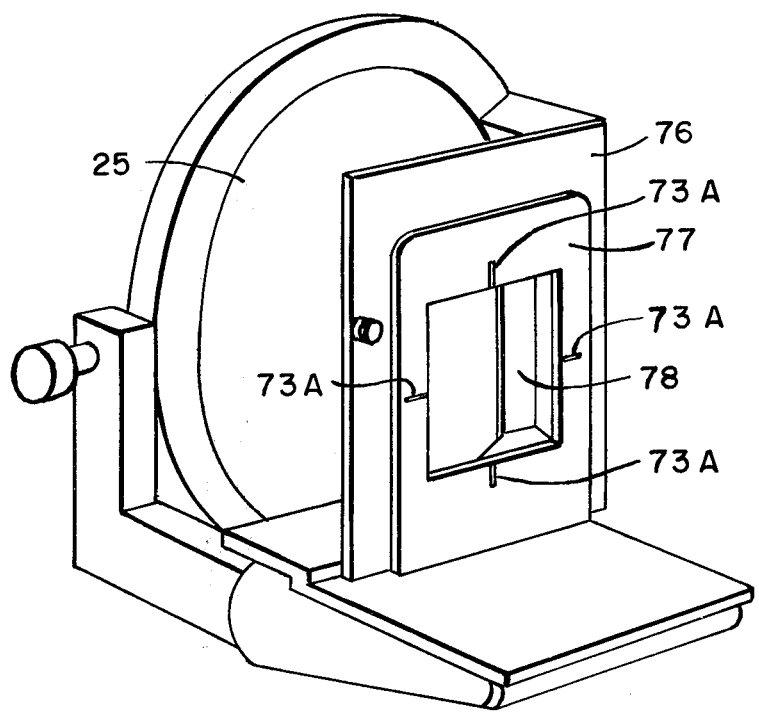
FIG. 4 is a perspective view of apparatus for mounting the individual radiographic perspectives in producing the holographic recordings according to FIG. 3.

Turning now to FIGS. 2 and 4, in order to reproduce the original radiographic recording geometry while holographically recording the several radiographic perspectives on the holographic medium 35 of FIG. 3, as disclosed above, it is desirable that the orientation of the radiographic perspectives 15A be reproduced exactly as they were originally recorded. Many methods may be used to accomplish this result, but one method is illustrated in FIGS. 2 and 4. Referring to FIG. 2, the object is again designated by reference numeral 10. The object 10 is bonded to a plate 72 which is transparent to the radiation from source 11, together with a number of wires designated 73. The wires 73 are radio-opaque. Thus, when an individual radiographic perspective is made, the images which result from the wires 73 provide fiducial marks on the resulting radiographic perspective. These fiducial marks are then used in the holographic recording process to orient each individual radiographic perspective 15A in FIG. 3 relative to the others.

One mechanism which may be used for orienting the individual radiographic perspectives is shown in FIG. 4. An indexing head generally designated 76, comprising a frame with a suitable aperture on which is mounted a reference radiograph 77 bearing fiducial marks only, the fiducial marks being designated 73A. The central portion of radiograph 77 has been cut out leaving an aperature 78, through which subsequent radiographs are illuminated after alignment as shown in FIG. 3. As each individual radiographic perspective is used, its fiducial marks are lined up with those of reference radiograph 77 mounted on the indexing head, so that all sequential radiographic perspectives bear the same relation to each other. The previously discussed ray back-tracing lens 25 may also be seen in FIG. 4. If the radiographic perspectives do not bear the same relation to each other as was maintained during their production, resolution will be lost in the final real image.

The foregoing discussion has assumed that a full scale reproduction is made. However, it is contemplated that a scaled version of the geometric dimensions may equally well be used either to produce a true scaled reconstructed three-dimensional real image or a reconstructed real image that embodies different scaling in different directions. Also the advantage of well known holographic reconstruction procedures could be used to produce different scaling in different directions. It is contemplated that this method be adopted to a situation in which the source of penetrating radiation is a collimated beam rather than a point source. In addition, radiographs that have been modified by familiar optical processing techniques such as spatial frequency filtering and deblurring would be advantageous in many instances.

If a collimated beam of radiation (such as neutrons) is used to irradiate an object to make the radiographs in FIG. 1, the path of the rays must be re-traced in making the holographic recording in FIG. 3. In the case of a collimated radiation source, the object beam would also be collimated.

Having thus described in detail one embodiment of the invention, persons skilled in the art will be able to substitute equivalent steps for those disclosed and to modify the equipment illustrated while continuing to practice the principle of the invention. It is, therefore, intended to cover all such modifications and equivalents within the spirit and scope of the appended claims.

We claim:

1. In a method of reconstructing a three-dimensional real image of an object, including preparing a plurality of radiographic images of said object, each from a different perspective, the improvement comprising: generating a reference beam of coherent light; generating an object beam of coherent light; passing said object beam of coherent light through ray back-tracing lens means and through said radiographic images to converge the same at a point on a path corresponding to the original path of rays used in irradiating said object with a source of penetrating radiation; illuminating a radiographic perspective with said converging object beam; and intercepting said converging object beam and said reference beam with a section of holographic recording medium between said path and said radiographic perspective for each of said radiographic perspectives, to thereby form a holographically-recorded image of each radiographic perspective containing the same perspective information in the original radiograph perspective.

2. A method of reconstructing a three-dimensional real image of a radiopaque object comprising: preparing a plurality of radiographs of said object by passing a source of penetrating radiation along a known path and irradiating said object at each of a plurality of positions along said path to prepare a plurality of radiographic perspectives; generating an object beam of coherent light and illuminating said radiographic perspectives therewith to re-trace the rays thereof in accordance with the geometry in which each of said radiographic perspectives was originally made; generating a coherent reference beam; holographically recording each radiographic perspective on a holographic recording medium using said object and reference beam; and then simultaneously illuminating all of said holographically-stored images with the conjugate of said reference beam.

3. A method of reconstructing a three-dimensional real image of an object comprising: preparing a plurality of radiographs of said object, each from a different perspective by irradiating said object with a source of radiation transmitting rays along predetermined paths to a radiographic recording medium; generating a reference beam of coherent light; generating an object beam of coherent light; passing said object beam of coherent light through ray back-tracing lens means and through said radiographs to re-trace said predetermined paths along which said radiation rays were transmitted; illuminating a radiographic perspective with said object beam exposing a section of holographic recording medium to said object beam and said reference beam simultaneously for each radiographic perspective to thereby form a holographically-recorded image of each radiographic perspective containing the same perspective information in the original radiographic perspective; and then simultaneously illuminating all of said holographically-recorded images with a beam of coherent light that is the conjugate of the reference beam used to make said holographically-recorded images.

4. A method of producing a three-dimensional real image of a radiopaque object comprising: preparing a plurality of radiographic perspective views of said object by providing a reference beam of coherent light and an object beam of coherent light, and directing said object beam to converge along a known path corresponding to the path of the source used to prepare said radiographic perspective views; illuminating each radiographic perspective view with said object beam, each radiograph being spaced from said path at a distance corresponding to the distance from the source of radiation used to prepare said radiographic perspective views to the associated radiograph; exposing a portion of holographic recording medium to said object beam and said reference beam at a location between said path and a radiographic perspective view illuminated by said object beam; directing a beam of coherent light which is the conjugate of said reference beam on a plurality of said holographically-stored images simultaneously to thereby reconstruct a three-dimensional real image of said object.

* * * * *